(12) United States Patent
Ma et al.

(10) Patent No.: US 8,864,671 B2
(45) Date of Patent: Oct. 21, 2014

(54) METHODS AND SYSTEMS FOR COLOR FLOW IMAGING

(75) Inventors: Zhongwei Ma, Shenzhen (CN); Lei Li, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 257 days.

(21) Appl. No.: 13/240,648

(22) Filed: Sep. 22, 2011

(65) Prior Publication Data

US 2012/0078107 A1   Mar. 29, 2012

(30) Foreign Application Priority Data

Sep. 28, 2010   (CN) .......................... 2010 1 0503688

(51) Int. Cl.
*A61B 8/00* (2006.01)
*A61B 8/08* (2006.01)
*A61B 8/06* (2006.01)

(52) U.S. Cl.
CPC ................. *A61B 8/06* (2013.01); *A61B 8/5276* (2013.01); *A61B 8/08* (2013.01); *A61B 8/488* (2013.01)
USPC ......................................... 600/453

(58) Field of Classification Search
USPC .......................................... 600/407, 437–472
See application file for complete search history.

(56) References Cited

U.S. PATENT DOCUMENTS 5,042,491 A   8/1991   Amemiya
5,494,037 A   2/1996   Banjanin et al.

FOREIGN PATENT DOCUMENTS

| CN | 1561916 A | 1/2005 |
| CN | 101167656 A | 4/2008 |
| CN | 101214157 A | 7/2008 |
| CN | 101524284 A | 9/2009 |

OTHER PUBLICATIONS

Yasuhiko, Abe, "Description of the Flow Image Optimizer (FIO)," Worldwide Latest News of Ultrasound Medicine, China Contemporary Medicine, pp. 60-63, vol. 6, No. 12, Dec. 2000.
Wang, Pei Dong et al., "Non-stationary Clutter Rejection in Ultrasound Color Flow Imaging," China Journal of Biomedical Engineering, pp. 240-243, vol. 27, No. 2, Apr. 2008.

*Primary Examiner* — Elmer Chao
(74) *Attorney, Agent, or Firm* — Kory D. Christensen; Stoel Rives LLP

(57) ABSTRACT

Methods and systems for color flow imaging are provided.

13 Claims, 7 Drawing Sheets

METHODS AND SYSTEMS FOR COLOR FLOW IMAGING

CROSS-REFERENCE TO RELATED APPLICATIONS

This application claims the benefit of priority of Chinese Patent Application No. 201010503688.7, filed on Sep. 28, 2010, which is incorporated herein by reference in its entirety.

TECHNICAL FIELD

The following disclosure relates to ultrasound imaging and, more particularly, to methods and systems for color flow imaging.

SUMMARY OF THE INVENTION

A method for color flow imaging may include: transmitting a pulse; receiving a pulse echo; performing beamforming on the received pulse echo; performing quadrature demodulation on the signal obtained after the beamforming to acquire a complex signal; performing characteristic estimation on the complex signal to acquire tissue characteristic parameters; performing wall filtering on the complex signal to filter out low-speed tissue information; performing weighting processing on the tissue characteristic parameters to acquire dynamic threshold values; performing characteristic estimation on the complex signal after the wall filtering to acquire flow characteristic parameters; performing typical flow identification on the flow characteristic parameters to acquire a typical flow signal; performing typical motion artifact identification on an atypical flow signal after the typical flow identification to acquire a similar signal; performing identification processing on the similar signal according to the dynamic threshold values to acquire a flow signal similar to a motion artifact; synthesizing the typical flow signal and the flow signal similar to the motion artifact to acquire a complete flow signal; and mapping the complete flow signal to a color flow image for outputting.

DETAILED DESCRIPTION

Figure 1:
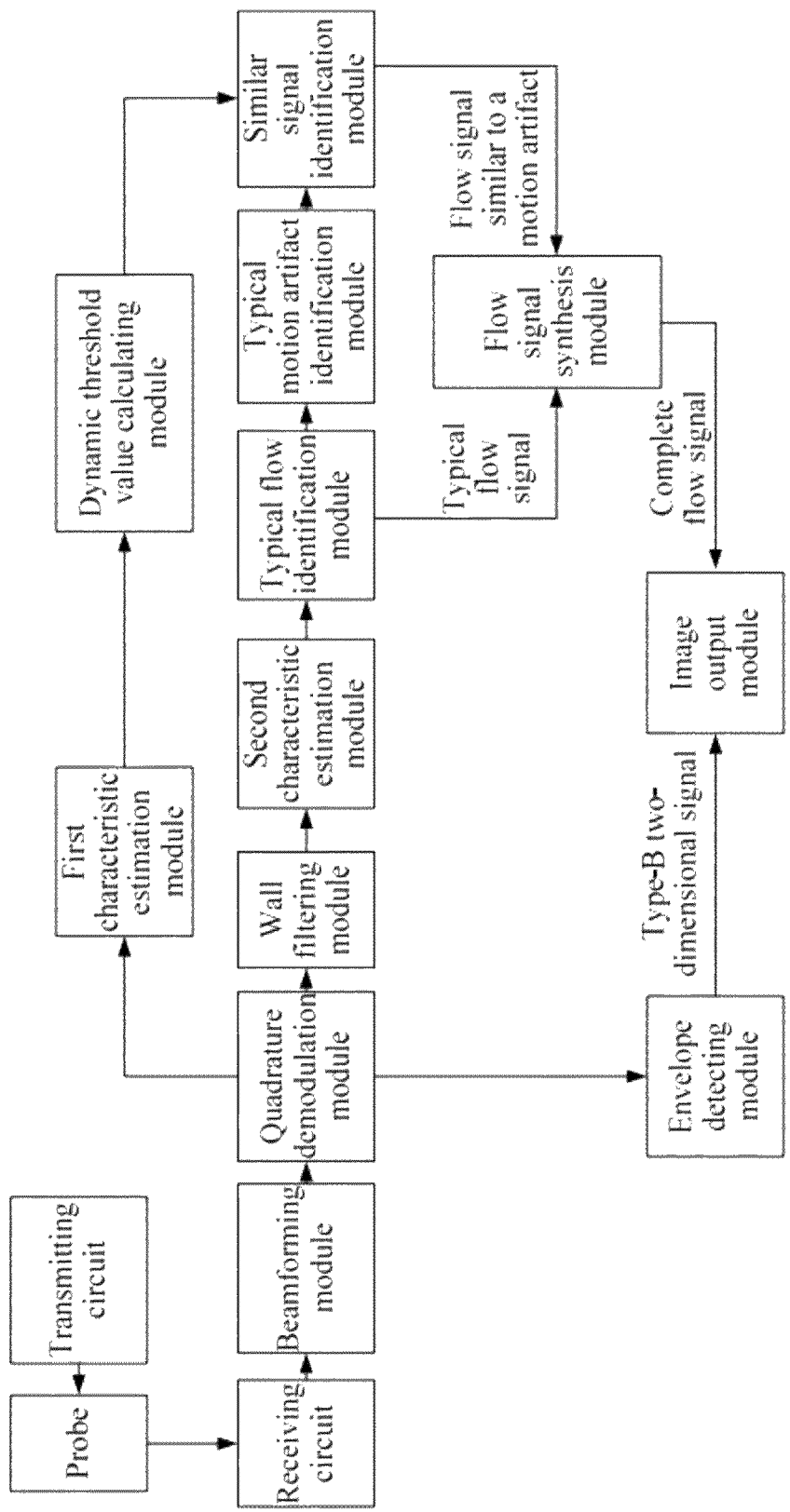
FIG. 1 is a block diagram of a color flow imaging system.

Ultrasonic waves are mechanical waves with frequencies higher than 20 kHz and are widely applied in medical diagnosis, ranging, and flaw detection. Medical ultrasound systems normally include various modules, such as a transducer, a transmitting/receiving circuit, and a digital signal processing module. Driven by the transmitting circuit, the transducer converts electric signals into ultrasonic waves and transmits the ultrasonic waves into human tissue. The ultrasonic waves propagate in the human tissue, and phenomena such as absorption, reflection, refraction, and scattering of the ultrasound waves may occur. A part of the scattered signals returns to the transducer and is converted back into analog electric signals. The receiving circuit converts the received analog electric signals into digital signals. By using digital signal processing, useful information is extracted and is converted into an image.

Ultrasonic waves propagate with different characteristics in different organs, which results in differences between energy of scattering echoes received by the transducer. The transducer transmits a pulse and then may capture a sequence of echo amplitude data indicating depths based on ultrasonic wave propagation speeds at different times. The transducer transmits multiple pulses to different positions in the same section of tissue so that a set of two-dimensional data indicating energy differences between ultrasonic wave scattering echoes of the different positions in the section may be acquired. The energy differences may be mapped to different gray scales of an image so that a two-dimensional monochrome image (referred to herein as a "two-dimensional image") is generated, which may illustrate structures of the human tissue.

During propagation of the ultrasonic wave, if a medium moves, the Doppler phenomenon occurs. If the medium moves towards the transducer, a frequency of a scattering echo increases; if the medium moves away from the transducer, the frequency of the scattering echo decreases. When detecting a Doppler effect, the transducer transmits a series of the same ultrasonic pulses to the same position in the tissue, and a pulse repetition frequency determines a maximum detectable movement speed of the medium. The blood flow moves continuously so that phases of adjacent pulse echoes may be different. Autocorrelation estimation is a common phase difference analysis algorithm, which may be used to estimate a speed, energy, and a variance from characteristics generated by the Doppler effect. Speed information acquired in the autocorrelation estimation may be mapped to pseudo-color information to generate a pseudo-color image, which may be referred to as a Doppler color flow image (hereinafter, a "flow image"). Energy information acquired in the autocorrelation estimation may also be mapped to pseudo-color information to generate a pseudo-color image, which may be referred to as an "energy image."

In medical ultrasonic diagnosis, a major moving medium that concerns a doctor is blood. However, besides the movement of the blood, the movement of tissue (e.g., breathing) may also generate the Doppler effect. Therefore, techniques are required to remove Doppler information that is not generated by blood movement so as to make diagnosis easier for the doctor. Normally, data acquired by autocorrelation is from three sources: ordinary noise, non-blood movement, and blood movement. When blood movement is being evaluated, the ordinary noise and the non-blood movement are not desired by the doctor. Causes for the ordinary noise are very complex and commonly include attenuation and reflection of a sound wave, inaccurate focusing, and circuit thermal noise. The ordinary noise is not incurred by the Doppler effect so that an energy value of the ordinary noise after wall filtering is low, and the ordinary noise may be identified by setting an energy threshold value. The noise incurred by the non-blood movement (such as breathing), movement of the myocardial wall, movement of tissues, movement of the probe, etc., is referred to as a "motion artifact," which is usually incurred by the Doppler effect. The signal incurred by blood movement is referred to as a "flow signal." Typical flow signals and typical motion artifacts have respective characteristics and may be discriminated. However, some flow signals and motion artifacts have similar characteristics (e.g., similar energy and speeds) so that it is difficult to remove the motion artifacts using conventional methods.

Flow identification technologies play an important role in medical ultrasound, and many methods are used to identify the flow signal. A most basic method is to set an energy threshold value. A signal having an energy value greater than the threshold value is identified as a flow signal, and a signal having an energy value smaller than the threshold value is identified as noise. The method affects the ordinary noise having low energy, but is not very useful in suppressing a motion artifact having high energy.

A second method is to increase a cutoff frequency of wall filtering, which has a suppressing effect on motion artifacts. However, frequencies of some motion artifacts are high, and the motion artifacts may not be completely filtered out by only increasing the cutoff frequency of wall filtering. In addition, it is also difficult to select a suitable cutoff frequency, and a cutoff frequency that is too high may filter out some low-speed flow signals.

A third method is to perform autocorrelation estimation twice on signals after quadrature demodulation, where wall filtering is performed in one autocorrelation estimation and is not performed in the other autocorrelation estimation. A comparison is conducted of the results of the two autocorrelation estimations so as to identify the motion artifact. The method may accurately identify a part of the motion artifacts, but, in some cases, a relationship exists between a flow signal before wall filtering and the flow signal after the wall filtering so that the method is likely to mistake the flow signal for a motion artifact, resulting in a wrong processing result.

In one embodiment of the disclosure, information after autocorrelation is divided into four types: ordinary noise, a similar signal (including a flow signal and a motion artifact having similar characteristics), an independent flow signal, and an independent motion artifact. The ordinary noise has low energy and may be identified according to an energy threshold value. The independent flow signal and the independent motion artifact are easily extracted, since the independent flow signal and the independent motion artifact have independent characteristics. For example, the independent flow signal has the characteristics of a high speed and medium energy, and the independent motion artifact has the characteristics of a low speed and high energy. For signals having independent characteristics, an accuracy rate of identifying the signals is very high, and the signals will have a high priority in identification. For the similar signal, comprehensive evaluation is required by using characteristics of the signal before wall filtering and characteristics of the signal after the wall filtering, and the flow signal is then separated from the motion artifact. Finally, the independent flow signal and the flow signal identified in the similar signal are integrated to acquire the final adequate flow signal.

Referring to FIG. 1, a color flow imaging system may include: a transmitting circuit for transmitting a pulse; a probe for converting the pulse into an ultrasonic wave, transmitting the ultrasonic wave, and receiving a pulse echo signal; a receiving circuit for amplifying the echo signal and performing analog to digital conversion on the echo signal; a beamforming module for performing beamforming on the received pulse echo; a quadrature demodulation module for performing quadrature demodulation on the signal obtained after the beamforming; an envelope detecting module for performing envelope detecting on the signal after the quadrature demodulation; a wall filtering module for performing wall filtering on the signal after the quadrature demodulation; a first characteristic estimation module for performing characteristic estimation on the signal after the quadrature demodulation; a dynamic threshold value calculating module for calculating a dynamic threshold value; a second characteristic estimation module for performing characteristic estimation on the signal after the wall filtering to acquire flow characteristic parameters; a typical flow identification module for performing typical flow identification on the flow characteristic parameters; a typical motion artifact identification module for performing typical motion artifact identification on the flow characteristic parameters; a similar signal identification module for identifying a flow signal in a similar signal; a flow signal synthesis module for synthesizing a typical flow signal and the flow signal similar to a motion artifact; and an image output module for generating a graph from a type-B two-dimensional signal and a complete flow signal and outputting the graph.

In one embodiment, the transmitting circuit, the probe, the receiving circuit, the beamforming module, the quadrature demodulation module, the wall filtering module, the second characteristic estimation module, and the typical flow identification module are connected in sequence. The typical flow identification module may be connected to the flow signal synthesis module. The typical flow identification module may be further connected to the typical motion artifact identification module. The typical motion artifact identification module may be connected to the similar signal identification module.

The quadrature demodulation module may be further connected to the first characteristic estimation module and the dynamic threshold value calculating module in sequence. The dynamic threshold value calculating module may be connected to the similar signal identification module. The similar signal identification module may be connected to the flow signal synthesis module. The quadrature demodulation module may be further connected to the envelope detecting module and the image output module in sequence. The flow signal synthesis module may be connected to the image output module.

In one embodiment, the transmitting circuit generates a transmission pulse, which is transferred to a transducer of the probe to be converted into an ultrasonic wave. The ultrasonic wave undergoes a series of physical processes in human tissue, such as refraction, reflection, and scattering, and a part of the energy returns to the transducer to be converted into an analog electric signal. The analog electric signal is converted into a digital signal through analog to digital conversion. The beamforming module effectively integrates signals received by array elements on the transducer and outputs a focused ultrasonic echo amplitude signal. The quadrature demodulation module converts the echo amplitude signal into a complex signal. Type-B two-dimensional image data is obtained by performing envelope acquisition on the complex signal.

Characteristic estimation may be performed on the complex signal directly to acquire tissue characteristic parameters. The characteristic estimation may be autocorrelation estimation, and the characteristic estimation may also be performed by using a Fast Fourier Transform (FFT), a Fourier transform, and/or an autoregressive model.

Another method for processing the complex signal is as follows. Wall filtering is performed on the complex signal before characteristic estimation is performed so as to acquire the flow characteristic parameters. The characteristic estimation may be autocorrelation estimation, and may also be performed by using an FFT, a Fourier transform, and an autoregressive model. Typical flow identification and typical motion artifact identification are performed on the flow characteristic parameters to acquire a similar signal. The similar signal not only includes flow signal data but also includes motion artifact data. During the typical flow identification, typical flow signal data may also be acquired. Weighting processing is performed on the tissue characteristic parameters to acquire a set of dynamic threshold values to identify a flow signal in the similar signal. Finally, the typical flow signal data and the flow signal data identified in the similar signal are synthesized to acquire complete flow image data. The image output module may display a type-B two-dimensional image and a flow image simultaneously.

In order to better acquire the tissue characteristic parameters, a low-pass filter may be added before the characteristic estimation is directly performed on the complex signal so as to keep tissue components and eliminate flow signal interference.

Figure 2:
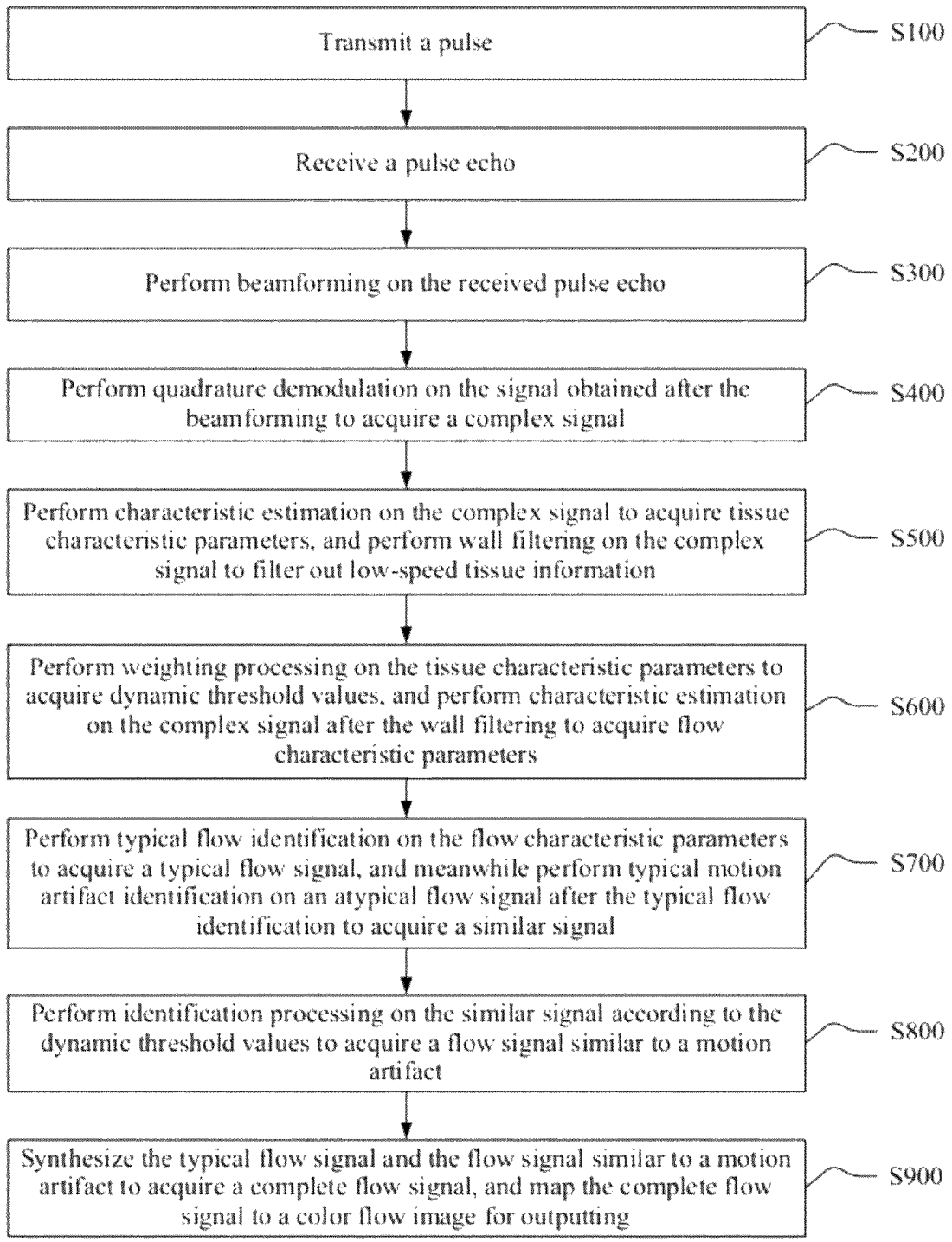
FIG. 2 is a flow chart of a color flow imaging method.

FIG. 2 is a flow chart of a color flow imaging method according to an embodiment of the disclosure. The method may include the following steps.

In Step S100, a pulse is transmitted.

In Step S200, a pulse echo is received.

In Step S300, beamforming is performed on the received pulse echo.

In Step S400, quadrature demodulation is performed on the signal obtained after the beamforming to acquire a complex signal.

In Step S500, characteristic estimation is performed on the complex signal to acquire tissue characteristic parameters, and wall filtering is performed on the complex signal to filter out low-speed tissue information.

In Step S600, weighting processing is performed on the tissue characteristic parameters acquired after the characteristic estimation to acquire dynamic threshold values, and characteristic estimation is performed on the complex signal after the wall filtering to acquire flow characteristic parameters.

In Step S700, typical flow identification is performed on the flow characteristic parameters to acquire a typical flow signal, and, meanwhile, typical motion artifact identification is performed on an atypical flow signal after the typical flow identification to acquire a similar signal.

In Step S800, identification processing is performed on the similar signal according to the dynamic threshold values to acquire a flow signal similar to a motion artifact.

In Step S900, the typical flow signal and the flow signal similar to the motion artifact are synthesized to acquire a complete flow signal, and the complete flow signal is mapped to a color flow image for outputting.

In some embodiments, the method may further include the following steps.

Envelope detecting processing is performed on the complex signal after the quadrature demodulation to acquire a type-B two-dimensional signal, and the type-B two-dimensional signal is mapped to a type-B two-dimensional image.

The type-B two-dimensional image and the color flow image may be displayed simultaneously.

Multiple methods may be used for performing the characteristic estimation on the complex signal to acquire the tissue characteristic parameters in Step S500. Autocorrelation is a common method for characteristic estimation of the Doppler effect. By performing autocorrelation estimation on the complex signal, parameter information including a speed, a variance, and energy may normally be acquired. In addition, an FFT, a Fourier transform, and/or an autoregressive model may also be used to perform the characteristic estimation of the Doppler effect. After the characteristic estimation is performed on the complex signal, ordinary noise filtering may be performed on the signal with a method in which an energy threshold value is set, and a signal with energy lower than the energy threshold value is filtered out. The ordinary noise processing may also be performed after the complete flow signal is synthesized and before the flow image is formed.

In addition, low-pass filtering may further be added before the characteristic estimation is performed on the complex signal to acquire more accurate tissue characteristic parameters.

Normally, tissue characteristics are dominant components, and if the characteristic estimation is performed directly, the tissue characteristic parameters may be acquired, which include a tissue speed, a tissue variance, and tissue energy. If the wall filtering is performed on the complex signal (the wall filtering is high-pass filtering or band-pass filtering, and is used to filter out low-speed tissue information) before the characteristic estimation is performed on the complex signal, another set of characteristic parameters may be acquired, which are often referred to as "flow characteristic parameters," including a flow speed, a flow variance, and flow energy.

Figure 3A:
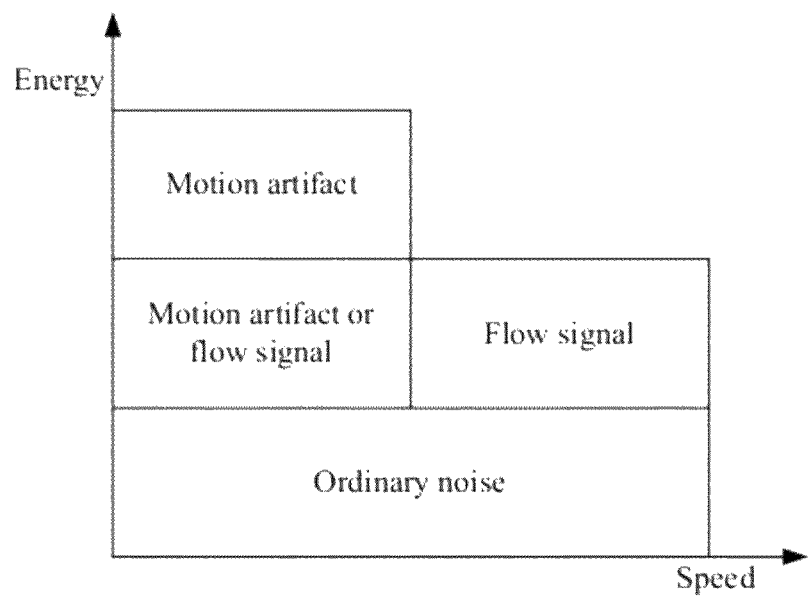
FIGS. 3A, 3B, 3C, 3D, and 3E are graphs of energy vs. signals after autocorrelation.

In one embodiment, information acquired after the high-pass filtering and the characteristic estimation includes, as shown in FIG. 3A, ordinary noise, the similar signal (including a flow signal and a motion artifact having similar characteristics), an independent flow signal, and an independent motion artifact. The ordinary noise has low energy and may be identified according to an energy threshold value. The energy threshold value may be set in any step after the autocorrelation and may also be set after the synthesis of the flow signal is completed.

Figure 3B:
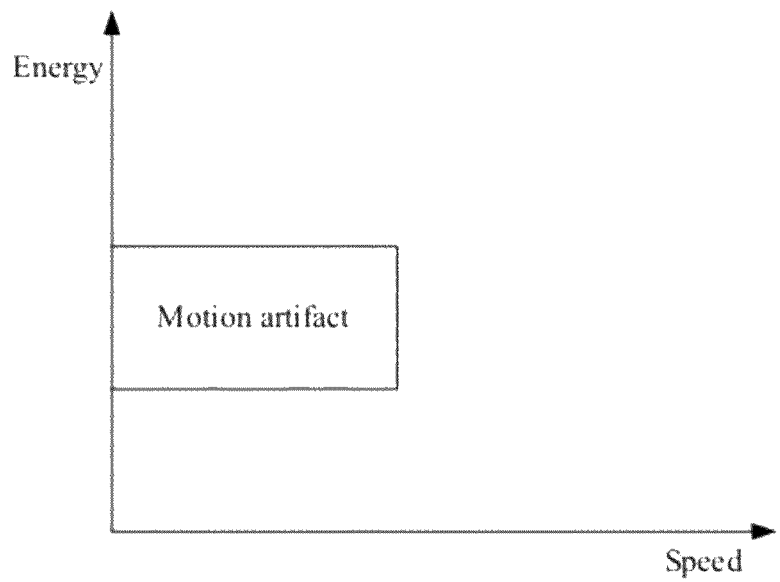
Figure 3C:
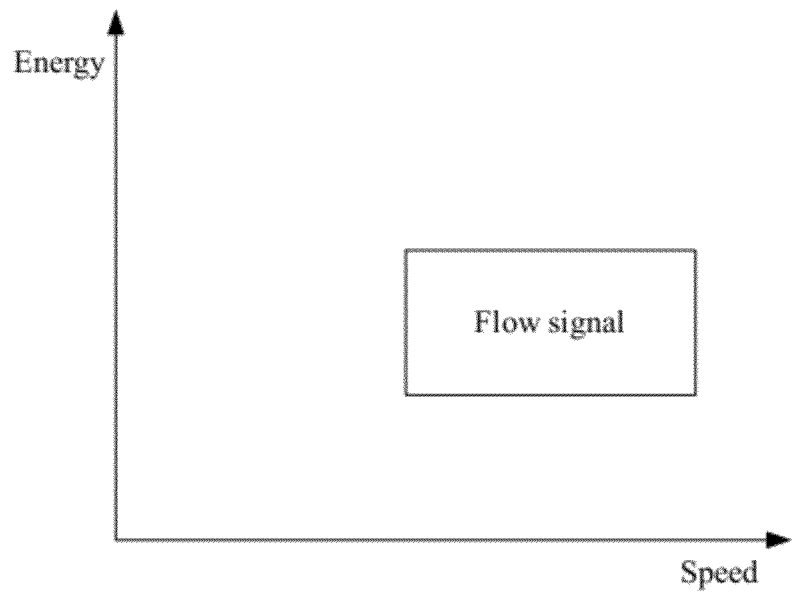
Figure 3D:
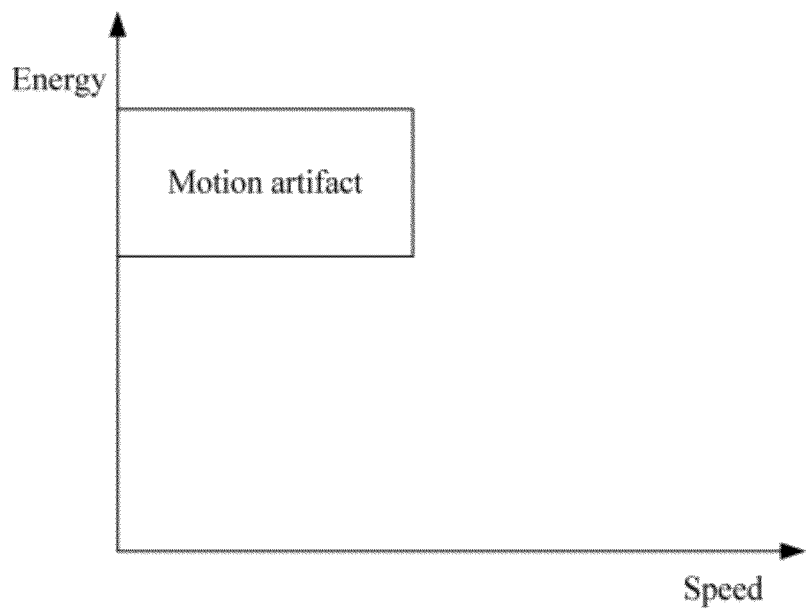
Figure 3E:
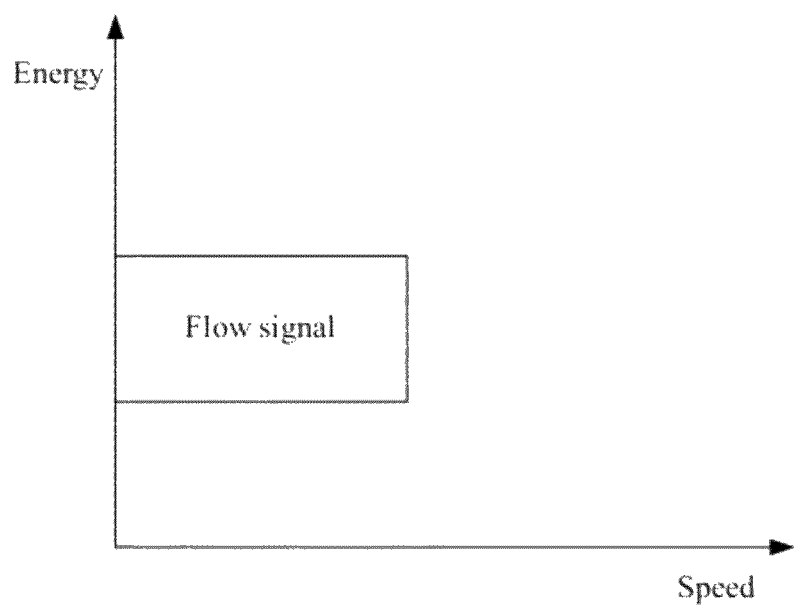

The independent flow signal and the independent motion artifact may be extracted separately, since the independent flow signal and the independent motion artifact have independent characteristics. For example, the independent motion artifact has characteristics, such as a low speed and high energy, and, as shown in FIG. 3B, may be identified by setting a speed threshold value and an energy threshold value. The independent flow signal has characteristics, such as a high speed and medium energy, and, as shown in FIG. 3C, may also be identified by setting a speed threshold value and an energy threshold value, as described below. For signals having independent characteristics, an accuracy rate of identifying the signals is very high, and the signals will have a high priority in identification. The similar signal may be decomposed into a motion artifact shown in FIG. 3D and a flow signal shown in FIG. 3E, and the motion artifact and the flow signal have similar speeds and similar energy ranges so that comprehensive evaluation must be performed on characteristics before the wall filtering and characteristics after the wall filtering to separate the flow signal from the motion artifact. In addition, a characteristic of variance may also be used to discriminate signals. Normally, the independent flow signal and the independent motion artifact both have a small variance (e.g., a normalized value is smaller than 0.5), and the ordinary noise has a large variance (e.g., a normalized value is greater than 0.5). The variance character of the similar signal is complex and is not easy to measure directly.

Figure 4A:
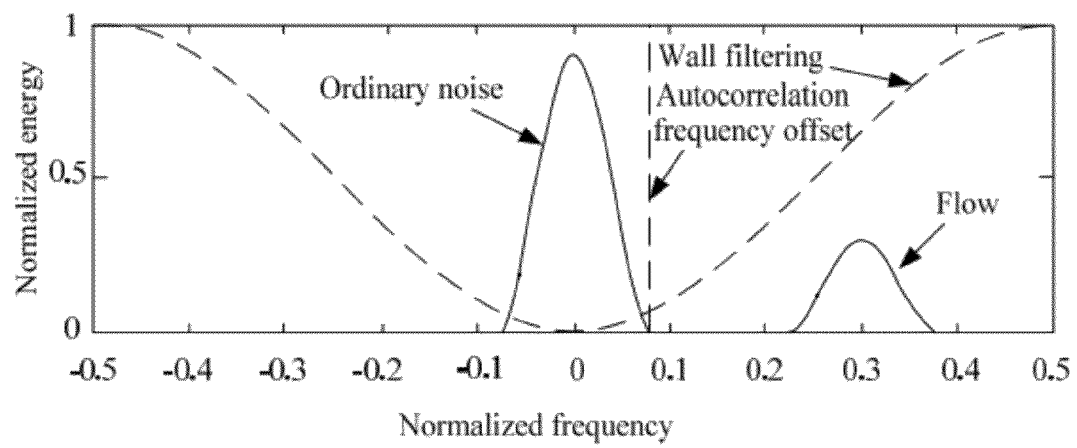
FIGS. 4A and 4B are views of normalized spectral characteristics of a flow signal before and after wall filtering.
Figure 4B:
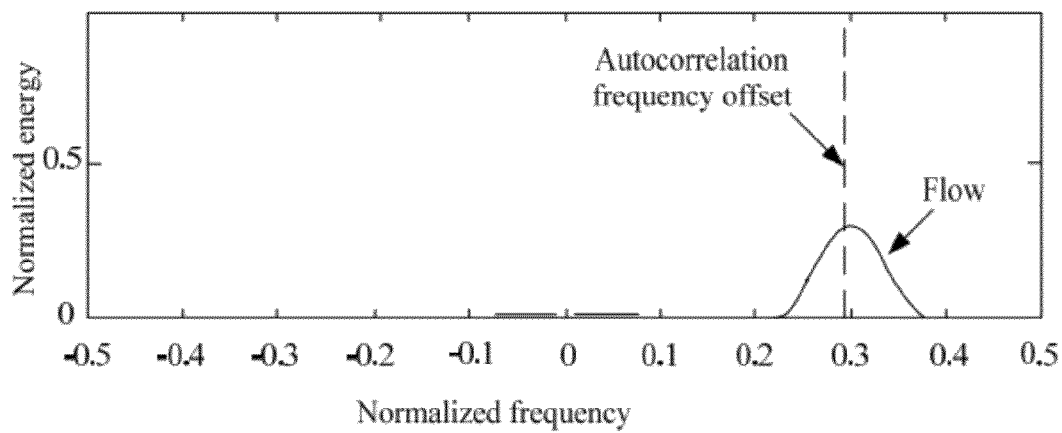
Figure 5A:
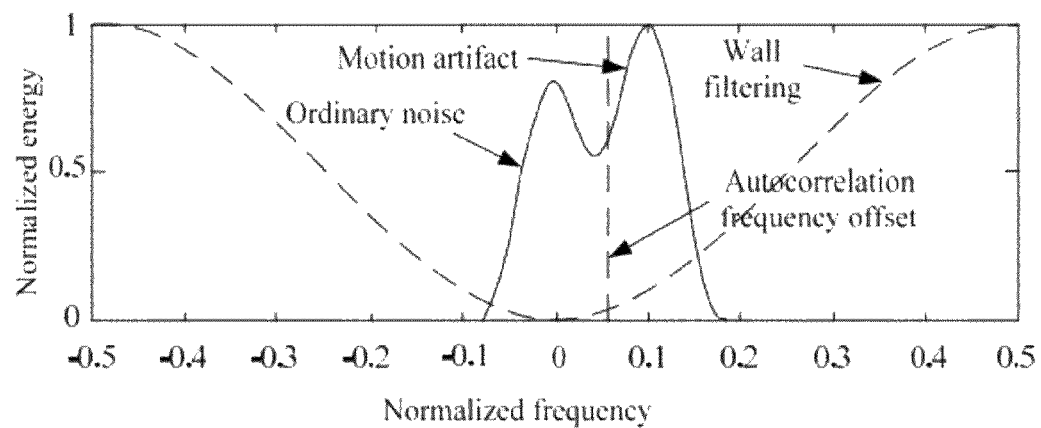
FIGS. 5A and 5B are views of normalized spectral characteristics of a motion artifact before and after wall filtering.

In order to identify the motion artifact and the similar flow signal correctly, differences between characteristics of the flow signal in the similar signal and characteristics of the motion artifact in the similar signal may be determined first. FIG. 4A shows characteristics of a flow signal having no motion artifact. Before wall filtering, ordinary noise is a dominant component. But after the wall filtering, as shown in FIG. 4B, the flow signal is a dominant component. FIG. 5A shows characteristics of a motion artifact with no flowing blood, and before the wall filtering, an ordinary noise and a motion artifact both affect the frequency offset estimation.

Figure 5B:
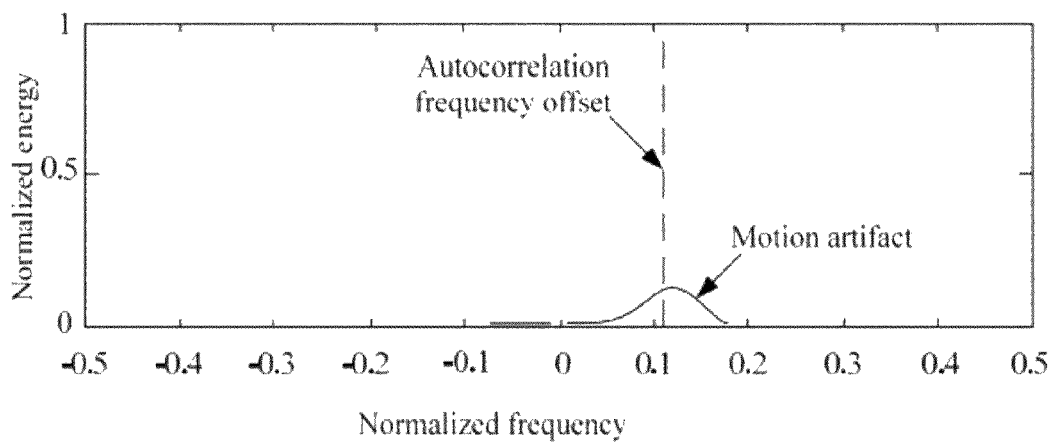

After the wall filtering, as shown in FIG. 5B, only motion artifacts that are not filtered out affect the parameter estimation.

After the wall filtering, if a speed value of a point is large (e.g., a normalized speed value is greater than 0.3) and energy is within a flow signal range, the signal may be regarded as an independent flow signal. The flow signal range is customized according to the actual system, and, for example, a normalized flow energy value ranges from 0.3 to 0.8. After the wall filtering, if the energy of a point is high and is significantly greater than the energy of a flow signal (e.g., a normalized energy value is greater than 0.8) and a speed value of the point is small (e.g., a normalized speed value is greater than 0.3), the signal may be regarded as an independent motion artifact. After the wall filtering, if energy of a motion artifact is similar to that of a flow signal, and a speed of the motion artifact (e.g., a normalized speed value is greater than 0.3) is also within a flow speed range, the signal is regarded as a similar signal, and a signal of this kind is identified by using a dynamic threshold value method, as described below. For example, in FIG. 4A and FIG. 4B, a difference between a speed value estimated before the wall filtering and a speed value estimated after the wall filtering is large. In FIG. 5A and FIG. 5B, a difference between a speed value estimated before the wall filtering and a speed value estimated after the wall filtering is small. Therefore, a tissue speed value estimated before the wall filtering may be used to calculate a dynamic speed threshold value to discriminate a motion artifact and a flow signal. In addition, tissue energy and a tissue variance may also be used to calculate dynamic threshold values to determine flow energy and a flow variance so as to analyze whether the signal is a flow signal.

Based on the differences in the characteristics of the flow signal and the motion artifact in the similar signal, a tissue speed value estimated before the wall filtering may be used to calculate a dynamic speed threshold value to identify the flow signal in the similar signal. In one embodiment, if a speed value after the wall filtering is greater than the corresponding dynamic speed threshold value, the signal is regarded as a flow signal; otherwise, the signal is regarded as a motion artifact, and the motion artifact is to be removed. Eventually, only the flow signal remains.

Due to the wall filtering, a tissue speed, a tissue variance, and a tissue energy undergo weighting processing before they correspond to a flow speed, a flow variance, and flow energy, that is, become matched in values. A method, such as aX+b, may be used to perform weighting, where X represents the speed, the energy, or the variance, and a and b are weighting parameters. In addition, a nonlinear method, e.g., aX2+bX+c, and a threshold value method may also be used to perform the weighting to acquire dynamic threshold value parameters.

Thus, when judging a motion artifact, weighting is performed on three physical parameters. In other words, the tissue speed, tissue variance, and tissue energy acquire three dynamic threshold values: a dynamic speed threshold value, a dynamic variance threshold value, and a dynamic energy threshold value. Using the three dynamic threshold values, a motion artifact and a similar flow signal may be identified correctly.

Taking FIG. 4A and FIG. 4B as examples, a tissue speed before the wall filtering (i.e., an autocorrelation frequency offset) is 0.075, a speed dynamic threshold value acquired after weighting by using 2× is 0.15, and after the wall filtering, the speed is 0.29, which is greater than a speed dynamic threshold value of 0.15. Therefore, the information is deemed a flow signal.

Taking FIG. 5A and FIG. 5B as examples, a tissue speed before the wall filtering (i.e., an autocorrelation frequency offset) is 0.06, a speed dynamic threshold value acquired after weighting by using 2× is 0.12, and after the wall filtering, the speed is 0.11, which is smaller than a speed dynamic threshold value of 0.12. Therefore, the information is deemed a motion artifact.

Finally, the independent flow signal and the flow signal identified in the similar signal are integrated to acquire a final adequate flow signal. The adequate flow signal may be mapped to a pseudo-color image by using speed characteristics, and may also be mapped to a pseudo-color image by using energy characteristics so that a Doppler color flow image is acquired. The Doppler color flow image and a two-dimensional image are superposed to form a final image to be displayed.

In the above description, numerous specific details are provided for a thorough understanding of the embodiments described herein. However, those of skill in the art will recognize that one or more of the specific details may be omitted, or other methods, components, or materials may be used. In some cases, operations or components are not shown or described where known to skilled artisans and to avoid obscuring more important details.

Furthermore, the described features, operations, or characteristics may be combined in any suitable manner in one or more embodiments. It will also be readily understood that the order of the steps or actions of the methods described in connection with the embodiments disclosed may be changed as would be apparent to those skilled in the art. Thus, any order in the drawings or Detailed Description is for illustrative purposes only and is not meant to imply a required order, unless specified to require an order.

Embodiments may include various steps, which may be embodied in machine-executable instructions to be executed by a general-purpose or special-purpose computer (or other electronic device). Alternatively, the steps may be performed by hardware components that include specific logic for performing the steps or by a combination of hardware, software, and/or firmware.

Embodiments may also be provided as a computer program product including a non-transitory machine-readable medium having stored thereon instructions that may be used to program a computer (or other electronic device) to perform processes described herein. The machine-readable medium may include, but is not limited to, hard drives, floppy diskettes, optical disks, CD-ROMs, DVD-ROMs, ROMs, RAMs, EPROMs, EEPROMs, magnetic or optical cards, solid-state memory devices, or other types of media/machine-readable medium suitable for storing electronic instructions.

Those of skill in the art would further appreciate that the various illustrative logical blocks, modules, circuits, and algorithm steps described in connection with the embodiments disclosed herein may be implemented as electronic hardware, computer software, or combinations of both. To illustrate the interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the invention as claimed hereinafter.

What is claimed is:

1. A method for color flow imaging, comprising:
transmitting, with a transmitting circuit, a pulse;
receiving, with a probe, a pulse echo;
performing, with a beamforming module, beamforming on the received pulse echo;
performing, with a quadrature demodulation module, quadrature demodulation on a signal obtained after the beamforming to acquire a complex signal;
calculating, with a first characteristic estimation module, tissue characteristic parameters based on the complex signal;
performing, with a wall filtering module, wall filtering on the complex signal to filter out low-speed tissue information;
performing, with a dynamic threshold value calculating module, weighting processing on the tissue characteristic parameters to acquire dynamic threshold values;
calculating, with a second characteristic estimation module, flow characteristic parameters based on the complex signal after the wall filtering;
determining, with a typical flow identification module, an independent flow signal based on the flow characteristic parameters;
determining, with a typical motion artifact identification module, a similar signal from first flow signals which are different from the independent flow signal after determining the independent flow signal;
determining, with a similar signal identification module, a second flow signal which has similar characteristics to a motion artifact from the similar signal according to the dynamic threshold values; and
synthesizing, with a flow signal synthesis module, the independent flow signal and the second flow signal to acquire a complete flow signal; and
mapping, with an image output module, the complete flow signal to a color flow image for outputting.

2. The method of claim 1, wherein, before mapping the complete flow signal to the color flow image, filtering out ordinary noise by setting an energy threshold value.

3. The method of claim 2, further comprising:
performing, with an envelope detecting module, envelope detecting processing on the complex signal acquired after the quadrature demodulation to acquire a type-B two-dimensional signal;
mapping, with the image output module, the type-B two-dimensional signal to a type-B two-dimensional image; and
displaying the type-B two-dimensional image and the color flow image simultaneously.

4. The method of claim 1, wherein calculating tissue characteristic parameters based on the complex signal comprises using an autocorrelation estimation method to calculate the tissue characteristic parameters based on the complex signal.

5. The method of claim 1, wherein calculating tissue characteristic parameters based on the complex signal comprises using a Fast Fourier Transform (FFT) estimation method, a Fourier transform estimation method, or an autoregressive model estimation method to calculate the tissue characteristic parameters based on the complex signal.

6. The method of claim 4, wherein the complete flow signal is mapped to pseudo colors by using speed characteristics to generate a color Doppler flow image.

7. The method of claim 4, wherein the complete flow signal is mapped to pseudo colors by using energy characteristics to generate a color Doppler flow image.

8. The method of claim 1, wherein, before calculating the tissue characteristic parameters based on the complex signal, low-pass filtering is performed on the complex signal to filter out flow signal.

9. The method of claim 8, wherein calculating tissue characteristic parameters based on the complex signal comprises using an autocorrelation estimation method to calculate the tissue characteristic parameters based on the complex signal.

10. The method of claim 8, wherein calculating tissue characteristic parameters based on the complex signal comprises using an FFT estimation method or an autoregressive model to calculate the tissue characteristic parameters based on the complex signal.

11. The method of claim 9, wherein the complete flow signal is mapped to pseudo colors by using speed characteristics to generate a color Doppler flow image.

12. The method of claim 8, wherein the complete flow signal is mapped to pseudo colors by using energy characteristics to generate a color Doppler flow image.

13. The method of claim 1, wherein the wall filtering is high-pass filtering.

* * * * *